United States Patent [19]
Errico et al.

[11] Patent Number: 5,643,265
[45] Date of Patent: *Jul. 1, 1997

[54] DYNAMIC COMPRESSION POLYAXIAL LOCKING SCREW PLATE ASSEMBLY

[75] Inventors: Joseph P. Errico, Hempstead, N.Y.; Thomas J. Errico, Summit; James Ralph, Oakland, both of N.J.

[73] Assignee: Fastenetix, L.L.C., Summit, N.J.

[*] Notice: The term of this patent shall not extend beyond the expiration date of Pat. No. 5,520,690.

[21] Appl. No.: 451,930

[22] Filed: May 26, 1995

Related U.S. Application Data

[63] Continuation-in-part of Ser. No. 421,087, Apr. 13, 1995, Pat. No. 5,520,690.
[51] Int. Cl.$^6$ .................................................. A61B 17/80
[52] U.S. Cl. .................................. 606/70; 606/69; 606/73
[58] Field of Search ............................. 606/61, 69, 70, 606/71, 72, 73, 66, 65, 60, 59, 54, 104

[56] References Cited

U.S. PATENT DOCUMENTS

| | | | |
|---|---|---|---|
| 3,779,240 | 12/1973 | Kondo | 606/69 X |
| 4,493,317 | 1/1985 | Klave | 606/69 X |
| 5,057,111 | 10/1991 | Park | 606/69 |
| 5,151,103 | 9/1992 | Tepic et al. | 606/69 |
| 5,395,371 | 3/1995 | Miller et al. | 606/61 |
| 5,429,639 | 7/1995 | Judet | 606/61 |
| 5,443,467 | 8/1995 | Biedermann et al. | 606/65 |
| 5,480,401 | 1/1996 | Navas | 606/61 |

OTHER PUBLICATIONS

"Cervi–Lok Cervical Fixation Systemo", Spinetich, Inc., 980 East Hennepin Ave., minneapolis, Minn 55414, 1994 Author Unknown.

"System Overview –Axis Fixation System", Sofamor Danek, 1800 Pyramid Place, Memphis Tenn 38132, 1994 Author Unknown.

"Surgical Technique –Orion Anterior Cervical Plate System", Sofamor Danek, 1800 Pyramid Place, Memphis Tenn 38132, 1994 Author Unknown.

"Surgical Technique –ZPlate–ATL Anterior Fixation System", Sofamor Danek, 1800 Pyramid Place, Memphis Tenn 38132, 1994 Author Unknown.

*Primary Examiner*—Guy V. Tucker

[57] ABSTRACT

A dynamic compression polyaxial locking screw plate assembly for reduction and/or drawing together, and immobilization, of displaced bone segments. The assembly comprises a plate, having an upper portion and a lower portion, at least one of which portions includes an elongate hole, into which hole a screw and coupling element is inserted. Complete insertion of the coupling element into the elongate hole causes the element to translate along sloped surface conformations of the lateral sidewalls, to a proximal end. This translation causes the bone segment into which the screw is inserted to translate relative to the plate. In a first embodiment, the coupling element has a tapered cylindrical exterior, and an interior semi-spherical concave surface in which the semi-spherical head of a bone screw may be polyaxially mounted. The plate of this first embodiment includes an axially widening, tapered sidewall conformation. In a second embodiment, the coupling elements include external annular flanges which mate in sloped channels in the sidewalls of the elongate holes. In a third embodiment, the lateral sidewalls of the elongate holes have inwardly curved lower lips which are sloped downward along the axial length of the elongate holes. The lower lips support the semi-spherical head of the corresponding screw without the aid of a coupling element. Additional round holes and holding screws are provided for additional securing strength after the compression has been provided.

9 Claims, 14 Drawing Sheets

DYNAMIC COMPRESSION POLYAXIAL LOCKING SCREW PLATE ASSEMBLY

CROSS-REFERENCE TO RELATED APPLICATION

This is a continuation-in-part application of U.S. Ser. No. 08/421,087, entitled "Anterior Spinal Polyaxial Locking Screw Plate Assembly" (Attorney Docket F-101), which was filed Apr. 13, 1995 now U.S. Pat. No. 5,520,690.

BACKGROUND OF THE INVENTION

1. Field of the Invention

This invention relates generally to an orthopedic implant assembly for holding and compressing together, adjacent bones, or bone portions. More particularly, this invention relates to a novel implant assembly for dynamically compressing adjacent bones together, wherein the dynamic compression is provided by polyaxial screws which may be locked to the plate.

2. Description of the Prior Art

Human bones are constructed of a hard external shell, referred to as cortical bone, and an interior which is less dense and is referred to as cancellous bone. Although bones are especially resilient and structurally remarkable with respect to the long term cycling of loading, which they are ideally constructed to support, a variety of trauma, as well as disease may cause bones to fracture. Bone fractures may be classified according to their severity, ranging from minor stress fractures to fully displaced fractures. Fractures are classified as "closed or "open", "open" describing those fractures wherein the skin is open and the fracture is exposed to the external environment.

Stress fractures, and other more mild bone breakage, occur when the bone develops a defect in its integrity, but otherwise is not structurally compromised in a gross manner. In healthy individuals, wherein the breakage is not causally related to a disease or other such pathology, stress fractures are often caused by excessive cyclical stress loading which exceeds the healing rate of the bone tissue. Such minor breaks, if not continuously aggravated, are generally treated by reducing the loading thereon for a short to intermediate period (a number of weeks). In some cases it is necessary to apply external immobilization to the bone or adjacent joints, in either a brace or a cast.

More serious fractures, including those in which the bone has a large structural defect, through those in which bone continuity is totally disrupted by a complete displacement of segments thereof, more drastic measures must be applied to correct the damage, and permit a "callus" to form around the bone to allow union of the fracture. In many cases it is sufficient to "set" the bone by initially placing the surfaces of the bone segments which need to be healed in contact with one another, and applying rigid external immobilization to protect the limb which has sustained the breakage. External casts and braces are utilized to provide stabilization of the bone, as well as to eliminate excessive stress loading during the healing process. Stress loadings of a light to moderate level are conducive to bone growth, however, if the stresses during healing are excessive, the fracture may not heal, and will alternatively go on to form a "non-union"

In more severe instances, however, the segments of the bone which is broken, and the manner in which the break manifests itself, makes the reduction of the fracture and the maintenance of the reduction difficult. In some cases the bone segments have been displaced to the extent that invasive surgical procedures must be carried out in order to openly reduce the bone segments together. In others, the specific bone which is broken (such as the femur or the hip) is one for which the time involved with total healing exceeds what may practically be externally immobilized for the duration. In still others, the ability of a cast to sufficiently relieve the loadings associated with a prudently constrained lifestyle is insufficient to permit correct healing. In these cases, and others, it is generally accepted that open reduction and internal fixation be provided, generally utilizing metal devices. Devices used for open reduction and internal fixation include screws, rods, and plates.

A very successful screw plate assembly, which has gained world-wide acceptance in the field of orthopedic surgery for the open reduction and internal fixation of long bone fracture is a dynamic compression plate (DCP). In its most widely used form, the DCP is an elongate planar metal plate having a plurality of sequentially spaced elongated holes, the holes being coaxial and extending along the axis of the plate. Each hole, which extends fully through the plate is defined by a pair of vertically oriented parallel sidewalls. The top of the parallel sidewalls, near the top surface of the plate, includes an additional recessed lip on which the annularly extending portion of the head of a screw rests once inserted into the hole. The top of the lip is, therefore, lower than the top surface of the plate. The elongate profile of the lip defines a downward slope with respect to the top surface of the plate, wherein the distance between the top of the lip surface and the top surface of the plate increases along the elongate axis of the hole. The downward slope of the lip of each hole is oriented toward the middle of the plate.

In use, the plate is positioned next to the exposed surface of the broken, and potentially displaced, bone such that one portion, an upper portion of the plate is adjacent one of the segments, and the holes of the other, lower portion, are adjacent to the other bone segment. First and second screws are inserted through the plate into opposing segments of the broken bone, at respective points along the axial extent of the elongate holes. It is preferred that the respective insertion points be at least some distance from the end of the hole having the lip at its greatest depth, herein referred to as the proximal end. In general, the screws are generally inserted at the uppermost end of the elongate holes, herein referred to as the remote end.

Once inserted, the screws are driven into the bone, therein securing the plate to the respective bone segments. The compressing function of the plate is utilized by continued driving of the screw into the plate once the annularly extending portion of the screw head has seated against the recessed lip of the hole. The downward force applied to the screw causes the head to slide down the slope of the recessed lip, thereby causing the bone in which it is inserted to move relative to the fixed plate. As the slopes of the respective holes are mutually directed toward the middle of the plate, the relative motion of the screws down the loped lips, and the corresponding motion of the bone segments into which they have been inserted, is together. The surgeon is thereby able to draw displaced bones together, and to hold the bones together internally during the required healing time.

It is understood that multiple elongate holes per side of the plate are an expedient for providing initial insertion sight choice to the surgeon, as full compression of one screw per side is the limit (further compression by a second screw per side would be prevented by the first). The additional holes may, however, be used to provide additional fixation points, effectively providing for the insertion of holding screws which help hold the plate to the bone.

Unfortunately, however, dynamic compression plates suffer from a failure mechanism which is endemic to all orthopedic implantation devices which incorporate bone screws. This failure mechanism is referred to as screw pull-out. Associated with screw pull-out are two complementary phenomena; the first being the failure of the screw-to-bone coupling, and the second being screw migration caused by repetitive cyclical loading. The failure of the screw-to-bone coupling is generally the result of loading, either in the form of a single sharp force which disrupts the sheath-like core of bone which surrounds the screw, or cyclical loading which weakens the bone sheath until it is too weak to hold the screw.

In most orthopedic implantation devices which are fixed via screws, the failure of the core of bone around a screw does not necessarily mean that the screw will pull out. If there are other screws which can hold he load for the period of time necessary for the bone coupling to reform, the fracture site may heal before the cyclical loading causes the screw to migrate. With respect to a dynamic compression plate, however, failure of the bone-to-screw interface is a particular problem as the constant lateral compression force which was applied via the head of the screw being driven down the slope of the lip is reversed. As the insertion holding strength of the screw is compromised the nearly uncontrollable tendency is for the screw to be lifted out of the hole as the bone segments slide back into displaced positions. This is an understandably critical problem as the failure of the bone-to-screw interface permits immediate pull-out, as well as potential catastrophic failure of the bone healing process.

While variations of the DCP concept, specifically those which include additional holding screws for anchoring the plate once compression has been applied, have reduced the dangers associated with bone screw pull-out in dynamic compression plates, the risks associated with this failure mechanism have not been eliminated. For example, the continued loading of the plate, even if fully secured, may still lead to the migration of the screw from the hole. In many areas of the body, the migration of a screw from an implantation device threatens collateral damage outside the obvious orthopedic implications, for example migrating screws may perforate adjacent vasculature or damage tissues.

An additional concern for surgeons who implant screw plate assemblies of all kinds is that a bone screw which is implanted perpendicular to the plate is particularly weak because the region of the bone which must fail for pull-out to occur is only as large as the outer diameter of the screw threads. It has been found that for pull-out to occur for a pair of screws which are angled inward, "toe nailed", or ones which diverge within the bone, and which are locked to the plate, the amount of bone which must fail increases substantially as compared to pairs of screws which are implanted in parallel along the axis that the loading force is applied. It has, therefore, been an object of those in the art to provide a screw plate assembly which permits the screws to be entered into the bones at angles other than 90 degrees.

With respect to dynamic compression plates, while the ability to drive additional holding screws in at angles other than 90 degrees is understandably valuable, the ability to drive the translating screw into the elongated hole at an angle other than 90 degrees (angled in the direction of compression) is especially important. The systems of the prior art which have provided for angulation of screws have generally been limited to single angles, via drill guides and offset surfaces for the angled heads to seat to. Surgeons ideally need to have freedom with respect to insertion angles so that the individual variations in fracture type, and bone anatomy may be accounted for in the fixation means. In addition, there are restrictions with respect to offset surfaces in that the screws associated therewith are not capable of dynamically compressing via travelling along an elongate hole; circular symmetry prevents proper seating in such a situation.

It is, therefore, a principal object of the present invention to provide a new and novel dynamic compression plate having a polyaxial coupling of the screw to the plate, and especially to the sloped lip of the elongated holes therein, whereby a single plate is compatible with a wide range of screw-in angles.

It is also an object of the present invention to provide a dynamic compression screw plate design having a locking compression screw and hole, whereby the screws which are inserted into the elongate holes are prevented from migrating out of the hole, despite potential bone-to-screw failure.

It is also an object of the present invention to provide a dynamic compression plate assembly which is more sturdy and more versatile than previous designs.

Further, it is an object of the present invention to provide a screw plate design which provides the surgeon with the greatest freedom to choose the most desirable angle to direct the bone screws.

It is also an object of the present invention to provide an orthopedic screw plate assembly which includes simple and reliable means for fixing the plate to the bone.

Other objects of the present invention not explicitly stated will be set forth and will be more clearly understood in conjunction with the descriptions of the preferred embodiments disclosed hereafter.

SUMMARY OF THE INVENTION

The preceding objects of the invention are achieved by the present invention which is a dynamic compression polyaxial locking screw plate assembly for use in compressibly holding segments of broken bones together and immobilizing same. The assembly comprises a plate having at least one (and preferably a pair) elongate hole, bone screws having a semi-spherical top portion, and coupling elements.

The plate is a flat metal element, having a rectangular shape with rounded corners, contoured to the curved cylindrical surface of the specific bone to which it is to be secured. In addition, it is desirable that the plate also comprise a plurality of round holes for receiving therethrough additional holding screws which are preferably polyaxial screws and coupling elements as are set forth in co-pending application U.S. Ser. No. 08/421,087, entitled "Anterior Spinal Polyaxial Screw Plate Assembly" (Attorney Docket No. F-101), the disclosure of which is herein incorporated by reference.

As described more fully in the above cited co-pending application the screws of the present invention have threading and shaft portions which may be of a variety of standard designs, or a particular design which may be found more secure than the standard ones. The head, however, is not standard in that it comprises a semi-spherical section.

For the purposes of inserting the screw into the bone, the head comprises a recessed region such as a slot, phillips, star, or hexagonal recesses which are ideally suited for mating to an appropriate screwdriving tool. The recess, however, shall not alter the exterior radially semi-spherical shape of the head.

The coupling element of this embodiment comprises a socket for holding the ball head of the screw, and an external conformation which permits the screw and coupling element to lockably mate with the sidewall morphology of the corresponding elongate hole. More specifically with respect to the sidewall morphology, in a first embodiment, the at least one elongate hole (preferably a pair of holes) extends in the direction of the elongate axis of the plate. The sidewalls of the elongate hole of this embodiment are tapered in two axes; the first axis being perpendicular to the plane of the plate, such that the hole is narrower at the bottom than at the top, and the second axis being coaxial with the hole itself, such that the hole is wider at the end closest to the middle of the plate (as measured with respect to the longitudinal axis of the plate), the proximal end.

The coupling element which corresponds to this first embodiment, therefore, comprises a cylindrical element, tapered to form a frusto-conical shape. The narrower bottom portion includes a hole which forms the mouth of an internal volume which is generally semi-spherical in shape, and sized to receive therein the ball head of the screw. In a preferred variation of this embodiment, the socket of the coupling element includes vertically oriented slots so it may be crush-locked to the ball head of the screw by the application of a radial force. In a highly preferred alternative variation, the coupling element comprises a single slot which extends the entire length of the coupling element; the coupling element therein comprising a ⅞ths ring. The width of the top of the elongate hole, at the remote end of the hole which is farthest from the middle of the plate, the remote end, is slightly wider than the diameter of the bottom of the coupling element, and is considerably narrower than the top of the coupling element. The tapered sidewalls of the plate widen in the direction of the middle of the plate, toward the proximal end wherein the width of the top of the elongate hole at the proximal end, is equal to the diameter of the top of the coupling element. The width at the bottom of the elongate hole widens as well, in the direction of the middle of the plate, however, at the proximal end, the width of the bottom of the hole widens at a slower rate than the top of the hole. It is this slight difference in tapering which compression locks the coupling element to the screw head and to the plate.

The first step in the process of implanting this embodiment of the invention is to position the plate against the segments of the broken bone which require compression and immobilization, and to align the entry points for the screws. The next step is to pre-drill holes into the bones at the desired position along the elongate hole, and angle with respect to the plate, into which the screws will be inserted. With the plate in position, the first and second screws are inserted through the elongate holes into the bone segments.

The coupling element must be partially open so that the screw may be easily manipulated, so that the recess in the head of the corresponding screw is accessible. Once the screw has been inserted into the bone, at the desired angle, the coupling element, via its rotationally free mating to the socket in the inserted screw, is realigned so that it may be seated in the elongated hole, the tapered surface of the coupling element fitted to the tapered walls of the hole. Continued rotation of the screw causes the coupling element to slide deeper into the hole, which correspondingly causes the screw and bone to be move relative to the plate. The coupling element continues to slide down the ever widening tapered walls of the hole, until it reaches the proximal end. At the proximal end, the slightly narrowed bottom of the hole crush locks the coupling element to the screw head, therein locking the screw to the coupling element, as well as compression locking the coupling element to the plate.

In a second embodiment, the elongate holes are not tapered along the axis which is perpendicular to the plane of the plate, but rather each sidewall comprises a sloped channel. This elongate hole does, however, retain a slight taper at the proximal end of the plate. At the remote end, the channel comprises only a recessed lower lip, the lip forming the lower extent of the lateral channel which is sloped downward into the plate. Once the channel has extended a distance large enough to provide an initial seating of the coupling element onto the lower lip, an upper lip portion, which defines the upper extent of the channel, is provided.

The coupling element of this embodiment comprises an annular flange which seats on the lower lip of the hole in an initial position, and is driven by continued insertion of the screw down the slope of the channel. Once the coupling element begins to translate down the channel, the upper lip extends over the annular flange and prevents the coupling element from pulling out.

Implantation of this apparatus is initiated in a manner which is generally similar to the first embodiment: the plate and holes are aligned, the pre-drill holes are provided at the appropriate angulations, the screws and their corresponding coupling elements are driven through the elongate holes and into the bone. Once the screw is inserted, and the annular flange of the coupling element seats on the lower lip of the channel and begins to translate down the slope in accordance with continued driving of the screw into the bone. The bone and screw move relative to the plate, both moving closer to the middle of the plate. As the annular flange of the coupling element travels, it becomes vertically locked beneath the upper lip of the channel. The tapering of the hole in the axial direction of the hole at the proximal end causes a radial compression of the coupling element, therein locking the ball head to the coupling element, in the same manner as the first embodiment (i.e. slots in the coupling element), but locking the screw to the plate via the annular flange and the channel.

A third embodiment of the present invention comprises a plate, similar to the ones described above, but wherein a coupling element is not utilized. In cross-section, the lower portion of the hole comprises an annular curved lip, forming a cup shaped support which is ideally suited for supporting the semi-spherical ball top of the screw while simultaneously permitting rotational motion whereby the entrance angle of the screw may be varied through a wide range. At the remote end of the elongate hole, the curved lip is disposed near to the top of the plate; at the proximal end of the hole, the curved lip is disposed near the bottom of the plate. Therefore, the elongate hole comprises a downward sloping curvate groove, into which the screw head may be rotationally free to slide downward.

The upper portion of the curvate groove includes a similarly curvate top portion at the proximal end, the top portion of the groove providing a vertical lock against pull-out.

In this third embodiment the screw is inserted through the appropriate hole of the properly positioned plate, into pre-drilled holes in the bone, until the ball head thereof seats against the curved lower lip of the groove. Continued rotation of the ball into the plate causes the head, and the bone into which the shaft has been inserted, to move relative to the plate, in the direction toward the middle of the plate. Once the screw has been driven as deeply as possible into the bone, and the screw head has reached the proximal end of the hole, the upper curved lip of the groove provides a vertical lock which provides against pull-out.

BRIEF DESCRIPTION OF THE DRAWINGS

Reference may now be had to the following detailed description of the various embodiments of the invention, taken in conjunction with the accompanying drawings; in which:

FIGS. 3a and 3b are top and side cross-section views of an elongate hole of a first embodiment of the present invention, wherein FIG. 3b is a cross-section of the plate along a plane perpendicular to the plate taken in the direction A—A as shown in FIG. 3a;

FIGS. 6a, 6b, and 6c are, respectively, a top view and side cross-sectional views of the plate of the second embodiment of the present invention, wherein the cross-section views of FIGS. 6b and 6c are taken along mutually perpendicular axes B—B and C—C as shown in FIG. 6a;

FIGS. 8a, 8b, and 8c are, respectively, a top view and side cross-sectional views of the plate of the third embodiment of the present invention, wherein the cross-section views of FIGS. 8b and 8c are taken along mutually perpendicular axes D—D and E—E as shown in FIG. 8a.

DETAILED DESCRIPTION OF PREFERRED EMBODIMENT

While the present invention will be described more fully hereinafter with reference to the accompanying drawings, in which particular embodiments are shown, it is to be understood at the outset that herein described while achieving the functions and results of this invention. Accordingly, the descriptions which follow are to be understood as illustrative and exemplary of specific structures, aspects and features within the broad scope of the present invention and not as limiting of such broad scope. Like numbers refer to similar features of like elements throughout.

Figure 1:
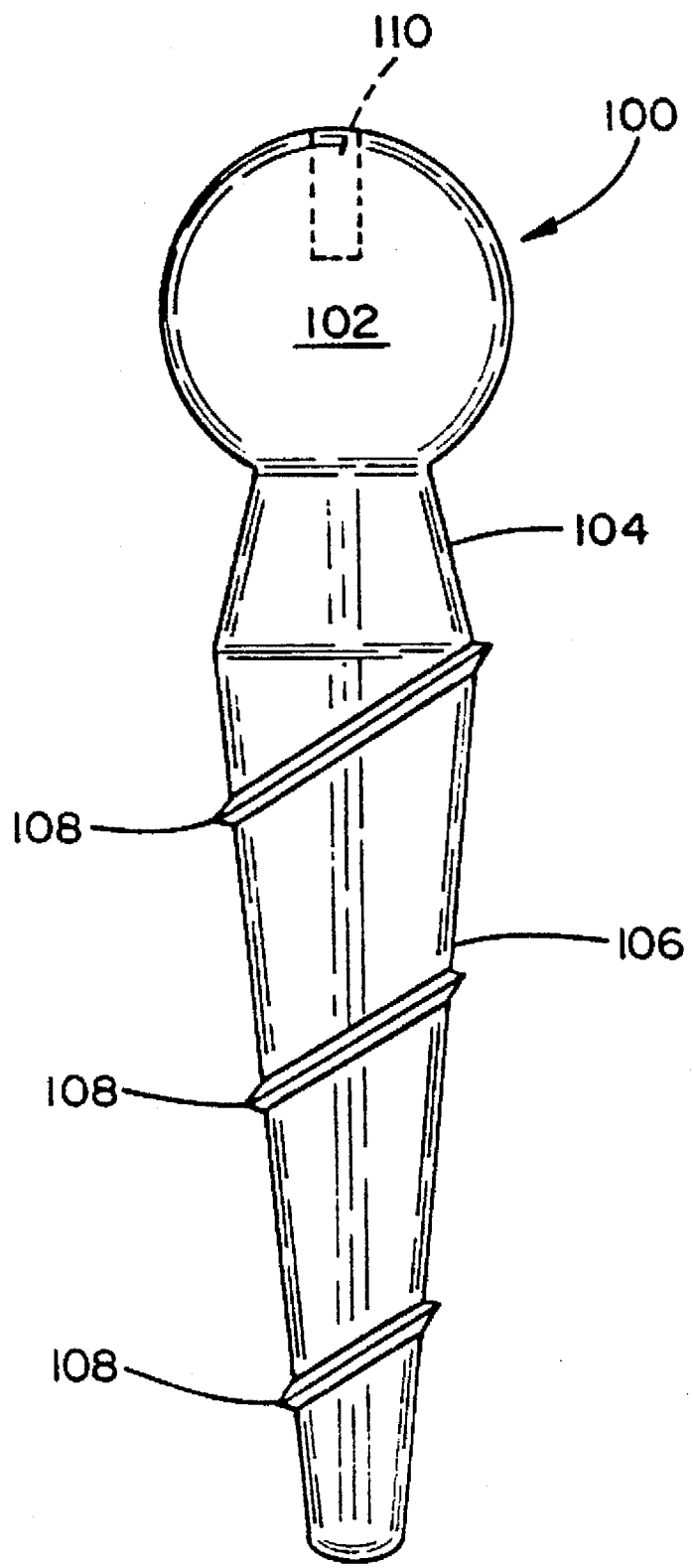
FIG. 1 is a side view of a bone screw which is an element of the present invention.

Referring now to FIG. 1, a screw of a type which is ideally suited for insertion into bone and fixation of aspects of the present invention thereto is shown in a side view. The screw 100 comprises a head portion 102, a neck 104, and a shaft 106. In FIG. 1, the shaft 106 is shown as having a tapered shape with a high pitch thread 108. It shall be understood that a variety of shaft designs are interchangeable with the present design. The specific choice of shaft features, such as thread pitch, or shaft diameter to thread diameter ratio, or overall shaft shape, etc. should be made by the physician with respect to the conditions of the patient's bone, however, this invention is compatible with a wide variety of shaft designs.

The head portion 102 of the screw 100 comprises a semi-spherical shape, which has a recess 110 in it. It is understood that the semi-spherical shape is necessarily a section of a sphere, greater in extent than a hemisphere, and is defined by an external surface which is equidistant from a center point of the head. In a preferred embodiment, the major cross-section of the semi-spherical head 102 (as shown in the two dimensional illustration of FIG. 1) includes at least 270 degrees of a circle.

The recess 110 defines a receiving locus for the application of a torque for driving the screw 100 into the bone. The specific shape of the recess 102 may be chosen to cooperate with any suitable screwdriving tool. For example, the recess 110 may comprise a slot for a flat-headed screwdriver, a crossed recess for a phillips head screwdriver, or most preferably, a hexagonally shaped hole for receiving an allen wrench. It is further preferable that the recess 110 be co-axial with the general elongate axis of the screw 100, and most particularly with respect to the shaft 106. Having the axes of the recess 100 and the shaft 106 co-linear facilitates step of inserting the screw 100 into the bone.

The semi-spherical head portion 102 is connected to the shaft 106 at a neck portion 104. While it is preferable that the diameter of the shaft 106 be less than the radius of the semi-spherical head 102, it is also preferable that the neck 104 of the screw 100 be narrower than the widest portion of the shaft 106. This preferable dimension permits the screw to be inserted at a variety of angles while still permitting the coupling element (as described with respect to FIG. 2) to be lockably mated with the elongate hole into which the screw and coupling element are inserted, while remaining coupled to the head 102.

Figure 2:
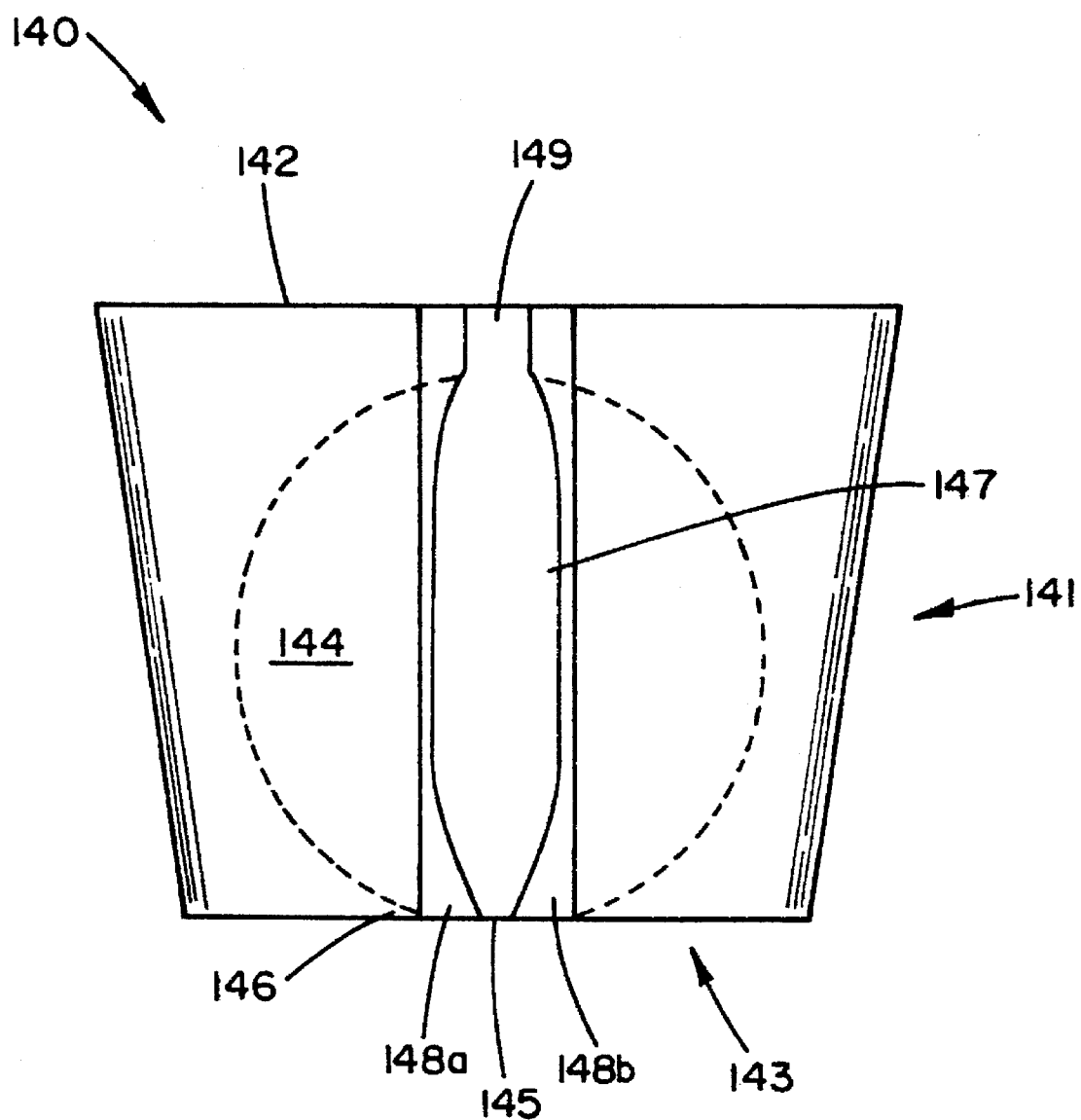
FIG. 2 is a side view of the coupling element which is an aspect of a first embodiment of the present invention.

Referring now to FIG. 2, a coupling element of the first embodiment of the present invention is shown in a side view, wherein phantom lines correspond to internal features of the coupling element taken along the diametric cross section. The coupling element 140 comprises a generally cylindrical body 141, having a tapered axial length, wherein the diameter of the top 142 of the element is wider than the bottom 143 of the element. The interior of the coupling element 140 comprises semi-spherical volume 144 which is ideally suited for holding the head portion 102 of the screw 100, and permitting the screw to rotate through a range of angles. The bottom 143 of the coupling element 140 has a has a circular hole (enumerated as 145 on the bottom surface 143 of the side view of the coupling element 140 in FIG. 2) which forms the bottom entrance into the interior semi-spherical volume 144. It is understood that the head 102 of the screw 100 is held within the interior semi-spherical volume 144 by an annular rim, or support lip, 146 of the bottom 143 of the coupling element 140. This annular support lip 146 defines the circular opening 145 which has a diameter less than the diameter of the semi-spherical head 102 of the screw 100.

It is, therefore, preferred that the coupling element 140 include an axial slot 147 which extends the entire length of the element 140. This slot interrupts the radial cross-section of the element, and extends from the elongate central axis to the cylindrical surface, therein rendering the element a ⅞ths ring. The head 102 of the screw can be inserted into the inner volume of the coupling element by expansion of the axial slot 147 via application of force against the inner surfaces 148a, 148b of the slot 147. Insertion of this coupling element into a hole tapered hole having a taper provides a radial closing force to the slot 147 which drives the inner surfaces 148a, 148b of the slot 147 together, therein further causing the coupling element 140 to lock to the screw head 102 under compression pressure.

The top 142 of the coupling element 140 further comprises a through hole 149, which extends from the top surface 142 to the interior semi-spherical volume 144. This through hole 149 is designed such that the screwdriving tool which is used to insert the screw 100 into the bone may access and rotate the screw 100 through the coupling element 140.

The coupling element 140 of this first embodiment is designed to fit into a sloped and tapered elongate hole, whereby the insertion of the screw 100 coupled therewith through the hole and into a bone segment beneath, followed by continued driving of the screw 100 into the bone, causes the coupling element to travel down the slope of the hole, therein moving the bone relative to the hole. Once the coupling has fully seated, a compressive force is applied by the walls of the hole, therein locking the ball head 102 of the screw 100 to the coupling element 140, and the coupling element 140 to the hole. The plate in which this elongate hole (a pair of elongate holes) is disposed is shown in FIGS. 3a and 3b.

Figure 3A:
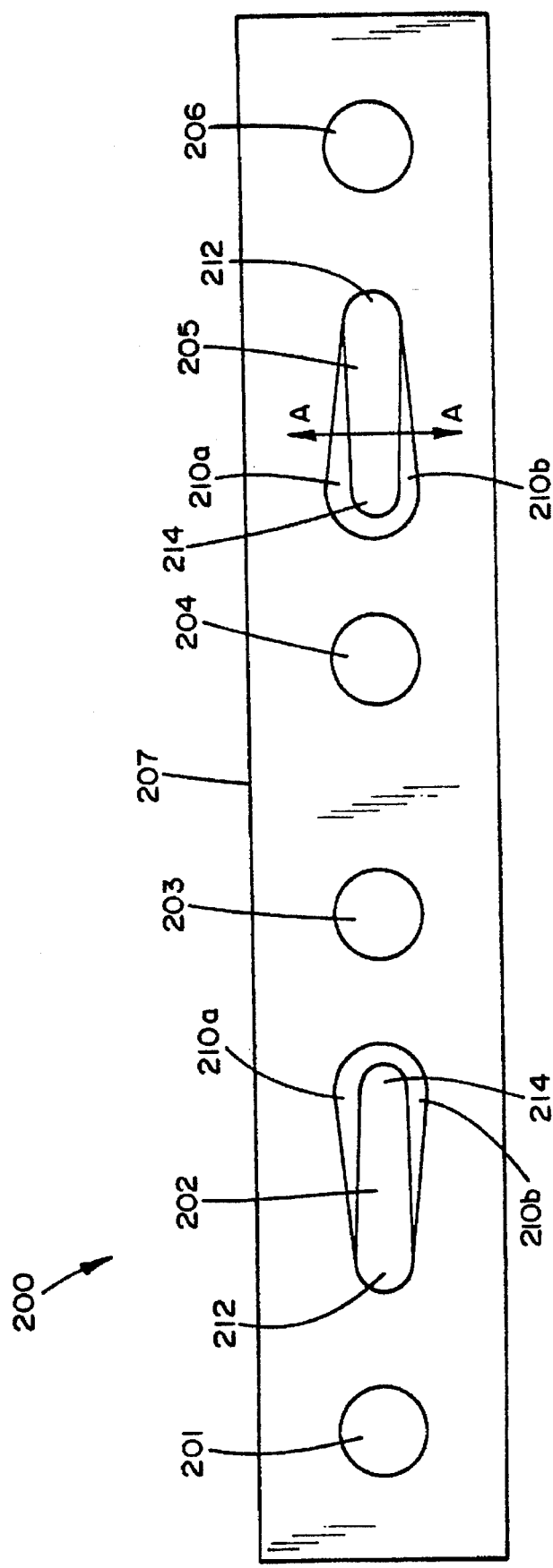
Figure 3B:
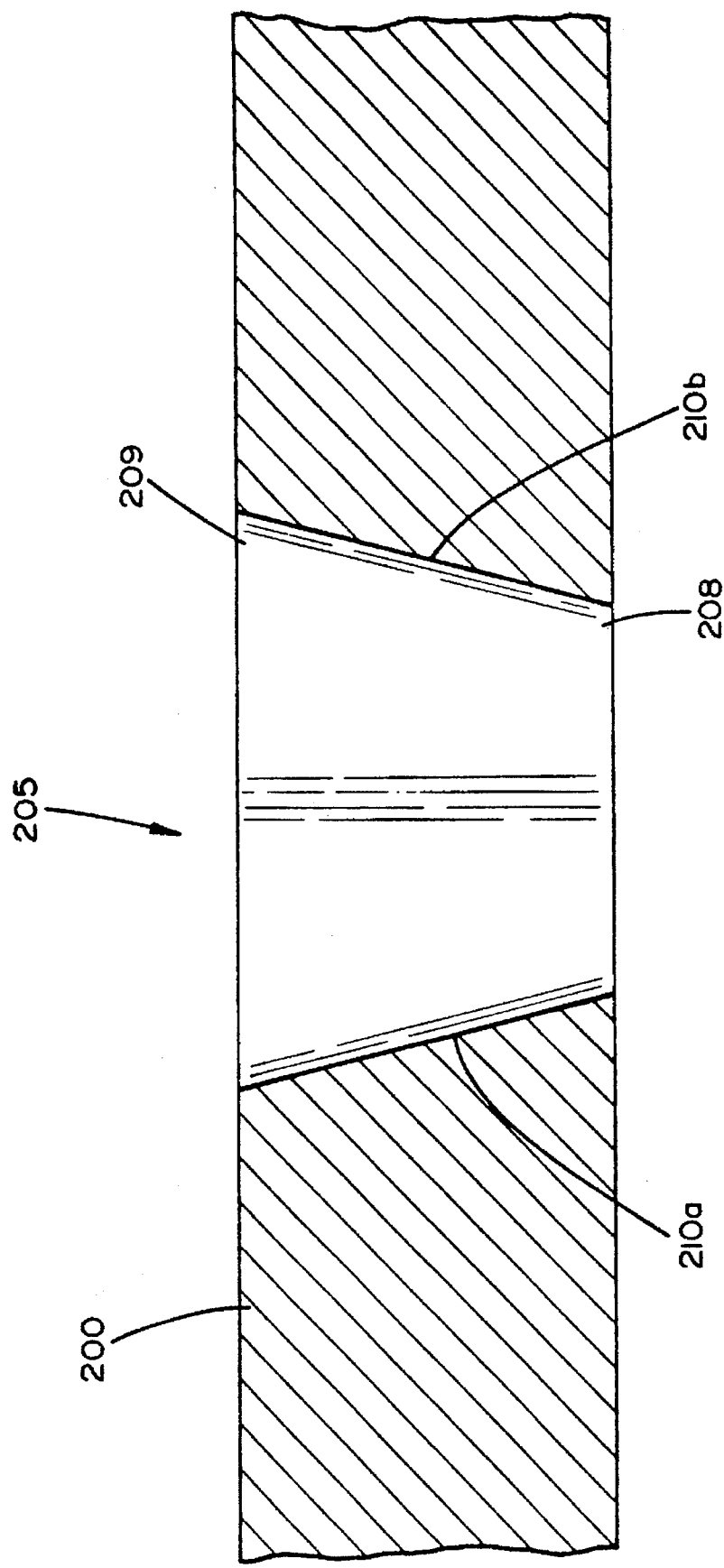

Referring specifically to FIG. 3a, a top view of the plate of the first embodiment of the present invention is shown wherein axis A—A is provided as a reference to a subsequent cross-section view provided in FIG. 3b. The plate 200 comprises an longitudinally extended, generally rectangular, thin metal plate, having a plurality of holes 201–206 defined therein. The holes 201–206 are divided into two groups of three, sequentially and symmetrically disposed on either sides of the longitudinal middle 207 of the plate. Holes 201, 203, 204, and 206 are provided for holding screws which provide additional securing strength once the initial affixation of the assembly, and the compression associated therewith, has been carried out. In this embodiment, holes 201, 203, 204, and 206 are round holes, for receiving therethrough a polyaxial screw and coupling element as set forth in the co-pending application U.S. Ser. No. 08/421,087, entitled "Anterior Spinal Polyaxial Locking Screw Plate Assembly".

Holes 202 and 205 are disposed on either side of the middle 207 of the plate 200, and are preferably equidistant therefrom. The holes 202 and 205 are oriented in opposite sense with respect to the middle 207 of the plate 200, such that remote ends 212 thereof are farther from the middle 207 than the proximal ends 214. These holes 202 and 205 are elongated in the longitudinal direction of the plate 200, having tapered sidewalls 210a, 210b.

More specifically with respect to the sidewall morphology, and referring also to FIG. 3b, the sidewalls 210a and 210b of the elongate hole 205 (or 202) are tapered along axes which are perpendicular to both the plane of the plate 200, and to the elongated sense of the hole 205. The width of the hole 205 is narrower at the bottom 208 than at the top 209. The taper of the hole 205 is such that the separation of the side walls 210a, 210b is wider at the proximal end 214 than at the remote end 212.

The frusto-conical shape of the coupling element 140, therefore, mates with the surfaces morphology of the elongate holes 202, 205. More specifically, the narrower bottom 143 of the coupling element 140 is slightly smaller than the distance between the sidewalls 210a, 210b of the top 209 of the elongate hole, at the remote end 212, which is in turn considerably narrower than the top 142 of the coupling element. The tapered sidewalls 210a, 210b of the plate 200 widen in the direction of the middle 207, such that the distance between the sidewalls 210a, 210b of the elongate hole 205 at the proximal end 214, are only slightly smaller than the corresponding tapered axial diameter of the coupling element 140. At the proximal end 214, it is this slight difference in tapering which provides the compression lock of the coupling element 140 to both the screw head 102 and the plate 200.

The first step in the process of implanting this embodiment of the invention is to position the plate against the segments of the broken bone which require compression and immobilization, and to align the entry points for the screws. The next step is to pre-drill holes into the bones at the desired position along the elongate hole, and angle with respect to the plate, into which the screws will be inserted. With the plate in place, one screw 100 and corresponding coupling element 140 are inserted through respective elongate holes 202, 207 into the bone segments. In this embodiment, the screws may be inserted at any point along the length of their corresponding holes 202, 205.

Once the screw has been inserted into the bone, at the desired angle, the coupling element 140, via its rotationally free mating of the socket 144 to the head 102 of the screw, is realigned so that it may be seated against the tapered surfaces 210a, 210b, in the elongated hole 202, 205. If the screw is inserted at a point which is not directly in the proximal end 214, for example at the extreme other end, the remote end 214, the seating of the coupling element 140 is not as deep as it could be. Continued rotation of the screw 100, therefore, causes the coupling element 140 to slide deeper into the hole, which correspondingly requires that the screw 100 and bone move relative to the plate 200. The coupling element 140 continues to slide down the ever widening tapered walls 210a, 210b of the hole, until it reaches the proximal end 214. At this proximal end 214, as the sidewalls 210a, 210b remain slightly narrower than the coupling element 140, continued driving of the screw into the bone causes the slot 147 to close, therein crush locking the coupling element 140 to the screw head 102, and further therein compression locking the coupling element to the plate.

Figure 4:
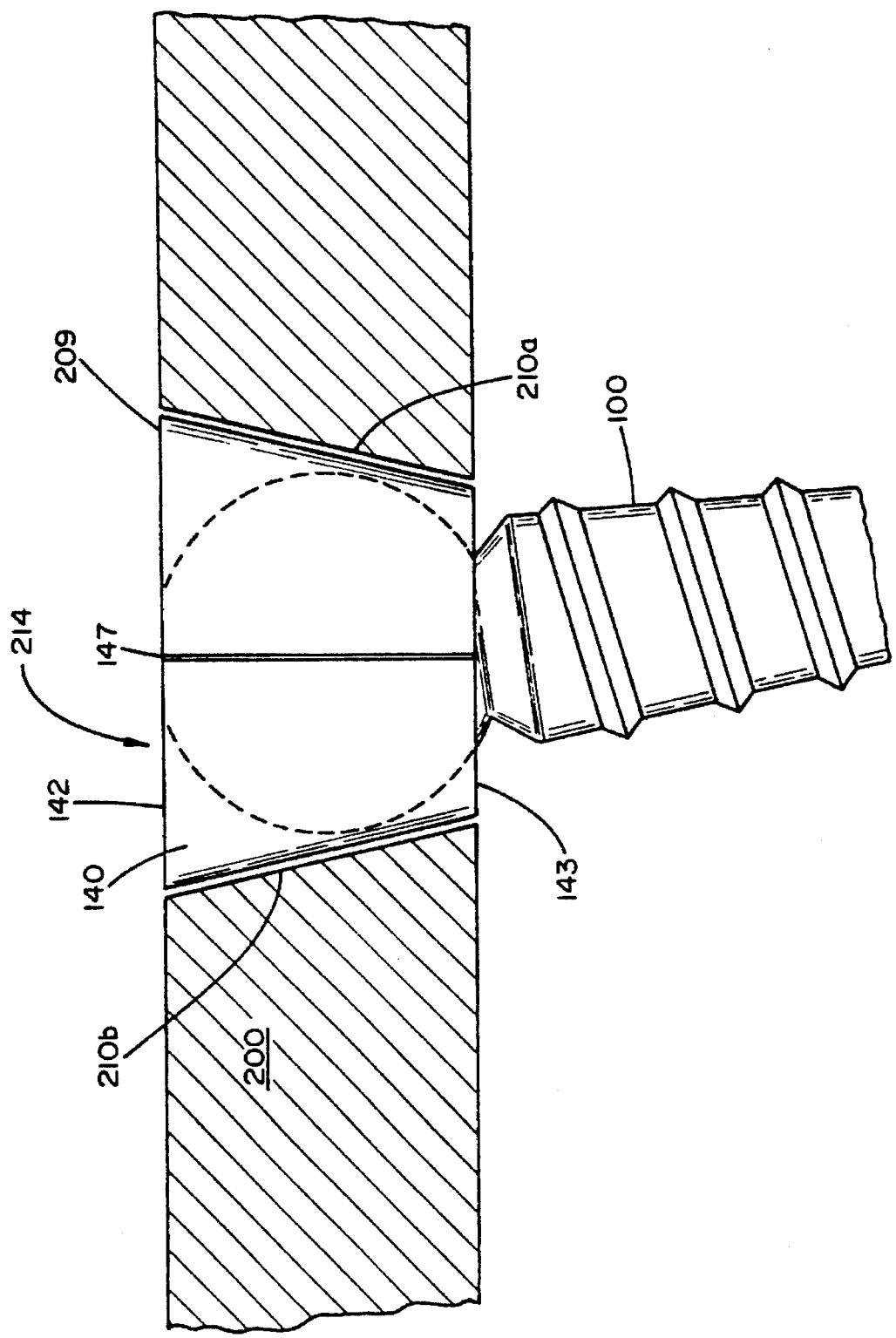
FIG. 4 is a side cross-section view of the seated and fully inserted implant assembly which is the first embodiment.

Referring now to FIG. 4, a cross-section view of the fully seated and locked screw 100 and coupling element 140 is shown. As stated above, and shown herein, the side walls 210a, 210b of the elongate hole 202, 205 are slightly narrowed so that the inner surfaces 148a, 148b of the slot 147 are forced together, therein crush locking the head 102 to the element 140, and compression locked to the plate 200.

Figure 5:
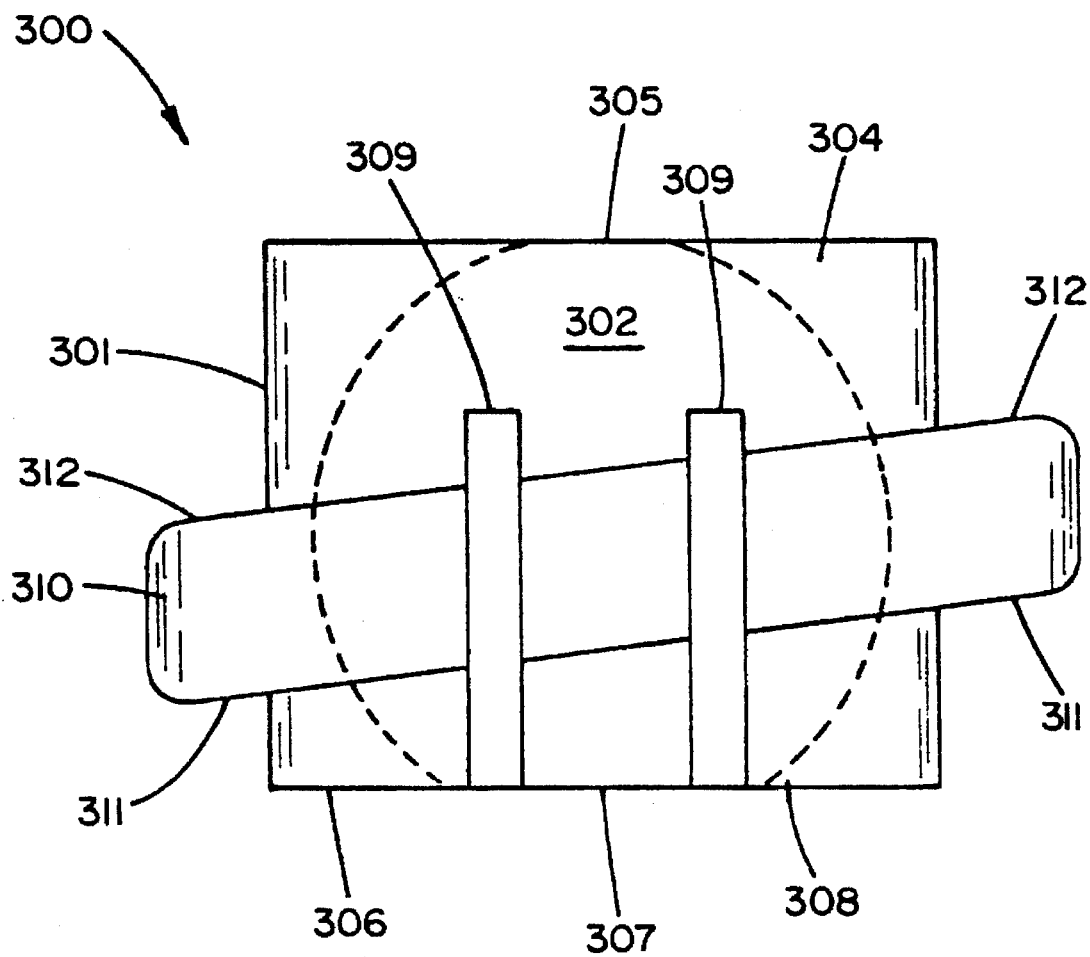
FIG. 5 is a side view of the coupling element which is an aspect of a second embodiment of the present invention.

Referring now to FIG. 5, the coupling element 300 of a second embodiment is shown in a side view. As in the coupling element of the first embodiment, the generally cylindrical body 301 of the element comprises an interior volume 302, into which the semi-spherical head 102 of a screw 100, such as is shown in FIG. 1, may be rotationally disposed. The top 304 of the coupling element comprises a hole 305 through which the surgeon may access the screwdriving hole in the head 102 of the screw 100. The bottom 306 of the coupling element 300 comprises a hole 307 through which the head of the screw may be inserted. The hole 307 has a diameter which is less than the major diameter of the screw head 102, so that the screw may be held therein. The mouth of the bottom hole 307, therefore, includes an annular lip 308 which prevents the ball head from escaping the inner volume 302. In order to provide a means by which the screw head 102 may be inserted into the coupling element 300, the bottom of the element 300 may include slots 309 which expand under the application of a radial force outward, therein expanding the mouth of the hole 307 to receive a larger diameter object therethrough. The slots 309 further permit the bottom 306 of the coupling element 300 to be compressed inward, locking the element to the head 102 of the screw, upon the application of a radially inward force.

The coupling element further comprises an annular flange portion 310 which extends outward from the cylindrical body. The flange 310 defines a circular ring which is offset slightly with respect to the axis of the coupling element body 301. The flange 310 has parallel upper and lower surfaces 312 and 311, respectively, and is ideally suited for travelling within a pair of parallel sloped channels as are described hereinbelow with respect to the corresponding plate of this embodiment.

Figure 6A:
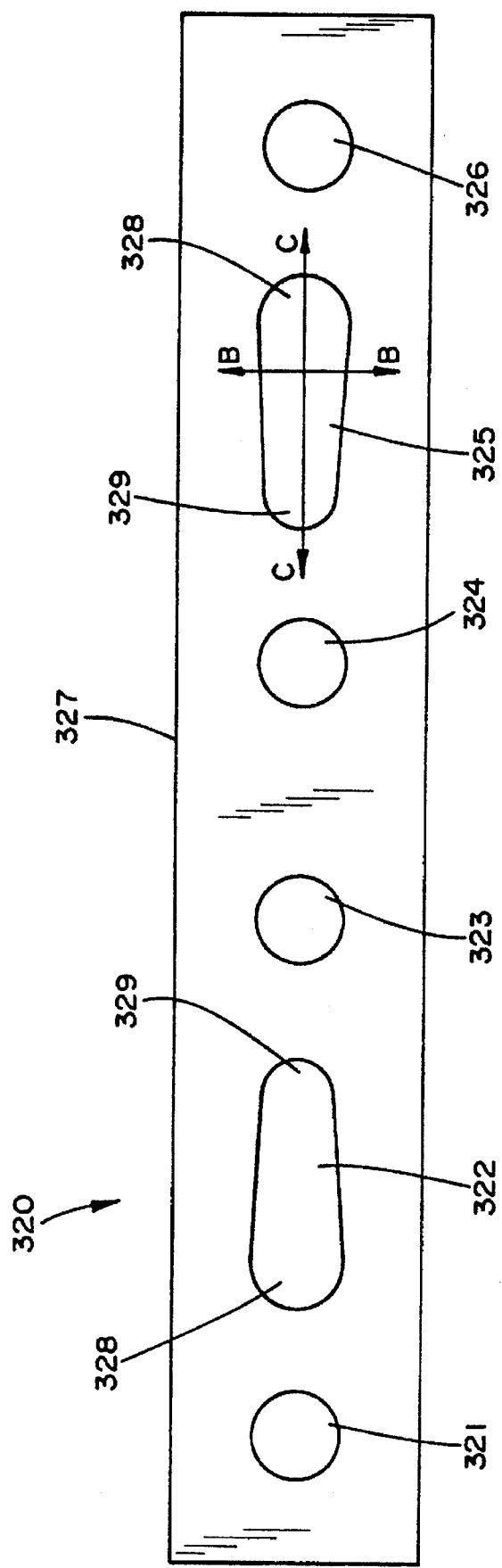
Figure 6B:
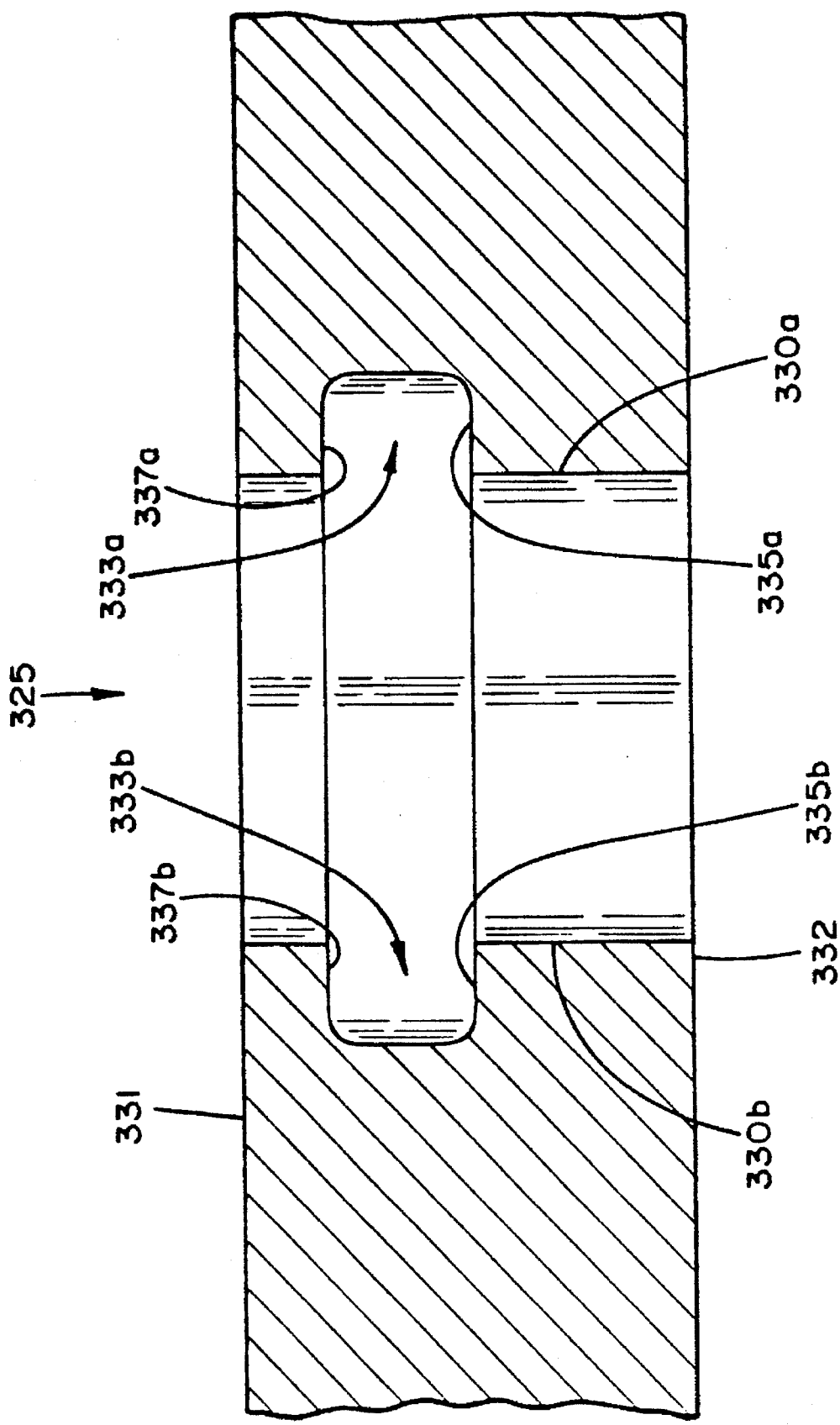
Figure 6C:
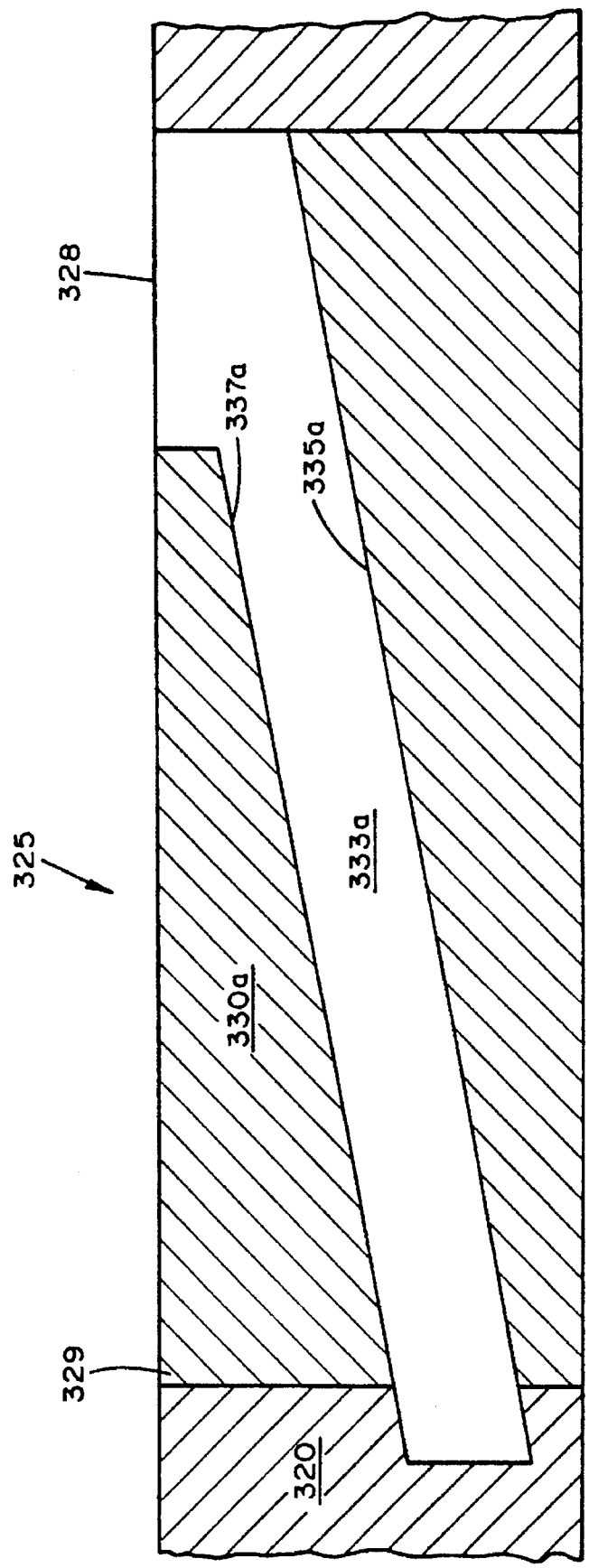

Referring now to FIGS. 6a, 6b, and 6c, the plate 320 of the present invention is shown in a top and two mutually perpendicular cross-sectional views. With specific reference to FIG. 6a, the plate 320 comprises a similar arrangement of through holes 321–326 as does plate 200 of the first embodiment. Two pair of round holes 321, 323 and 324, 326 are disposed in symmetric positions on either side of the middle 327 of the plate 320. These round holes, as above, are preferably designed to receive a screw and coupling element as disclosed in the co-pending application U.S. Ser. No. 08/421,087, the disclosure of which has been incorporated by reference. An elongate hole 322, 325 is disposed between each pair of round holes in either side of the plate 320. Each of the elongate holes has a wider remote end 328, farther from the middle 327 of the plate, and narrower proximal end 329. In this sense, as well as with respect to the conformation of the sidewalls of the elongate holes 322, 325, these holes differ from the elongate holes of the first embodiment.

More specifically, with respect to the surface morphology of the elongate holes 322, 325, reference is now made to FIGS. 6b and 6c. FIG. 6b shows the parallel sidewalls 330a, 330b of the elongate hole 325 (which is equivalent to elongate hole 322) according to the cross-section view along axis B—B shown in FIG. 6a. The sidewalls 330a, 330b comprise, respective, recessed channels 333a, 333b. The channels 333a, 333b include defining lower ledges 335a, 335b and upper ledge 337a, 337b.

As shown in FIG. 6c, which is a cross-section view of the elongate hole 325 (which is equivalent, but for a 180 degree switch in orientation, to the opposing elongate hole 322) along axis C—C of the plate 320, the channels 333a, 333b are sloped downward along the sidewalls 330a, 330b. At remote end 328 the channels 333a, 333b are open so that the lower ledge 335a, 335b may receive thereon the lower side 311 of the offset annular flange 310 of coupling element 300. The offset angulation of the flange 310 is ideally set to match the angulation of the sloped channels 333.

The initial steps of the implantation of the second embodiment of the present invention, including the preparation of the bone and the pre-drill holes, are similar to the preparatory steps associated with the first embodiment. Once positioned properly, the screws 100 are inserted in the bone through their respective elongate hole 322 or 325 until the corresponding coupling elements 300 have properly seated in the remote ends 328 of the elongate holes, with the lower surface 311 of the flanges 310 of each element 300 disposed on the lower ledges 335a, 335b of the channels 333a, 333b. From this point further, continued driving of the screw into the bone causes the flange 310 of the coupling element 300 to slide down the sloped channels 333a, 333b until the head has reached the deepest point at the proximal end 329. This translation of the coupling element down the channels 333a, 333b, necessarily causes the bone into which the screw has been inserted to move relative to the fixed plate. As the process is carried out in opposing directions by the oppositely oriented elongate holes 322, 325, displaced bone segments may be brought together and held fixed in contact.

Figure 7:
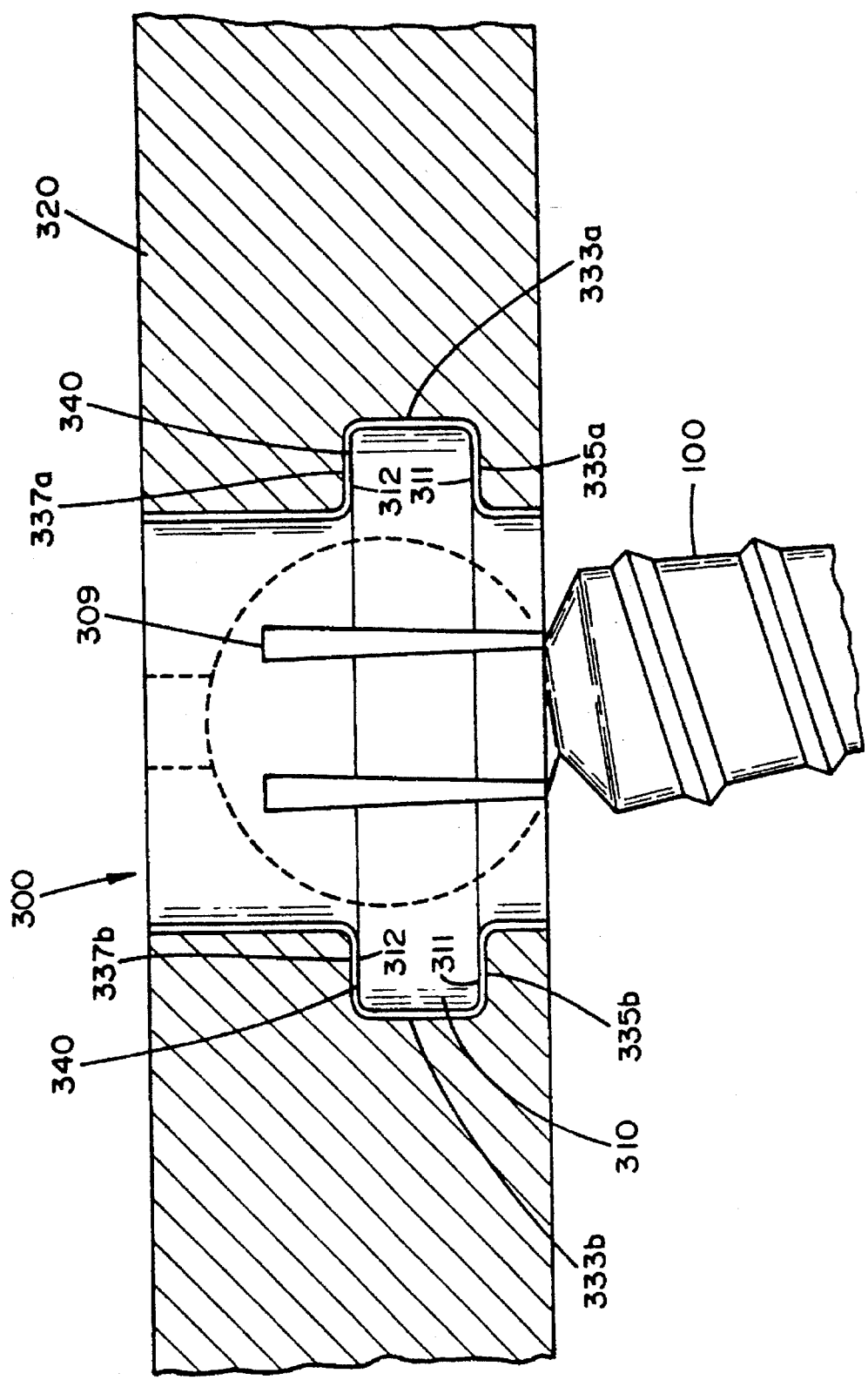
FIG. 7 is a side cross-section view of the seated and fully inserted implant assembly which is the second embodiment of the present invention.

In a preferred variation, the channels 333a, 333b narrow slightly along the longitudinal direction of the elongate hole, in the direction perpendicular to the axial direction of the elongate hole. This slight narrowing provides an inwardly directed radial force which causes slots 309 to close, thus locking the polyaxial screw 100 to the coupling element 300, so that it does not rotate with respect thereto. In all variations, however, it is preferred that the upper ledges 337a, 337b of each channel 333a, 333b in each of the sidewalls 330a, 330b provide contact surfaces against which the upper surface 312 of the offset annular flange 310 interfaces. This interface 340, as shown in FIG. 7, which illustrates the screw 100 and coupling element 300 in their fully inserted position, prevents screw back-out. In some variations, however, the upper ledges 337a, 337b are only provided at the proximal ends of the elongate holes 322, 325 so that the screws 100 and coupling elements 300 may be inserted at any point along the extent of the holes.

More specifically, FIG. 7 is provided to illustrate the coupling element 320 fully inserted in the plate 320, with offset annular flange 310 (which appears parallel in this cross-section angle) fully nested between the upper and lower ledges 312, 311, respectively, of the channels 333a, 333b.

Figure 8A:
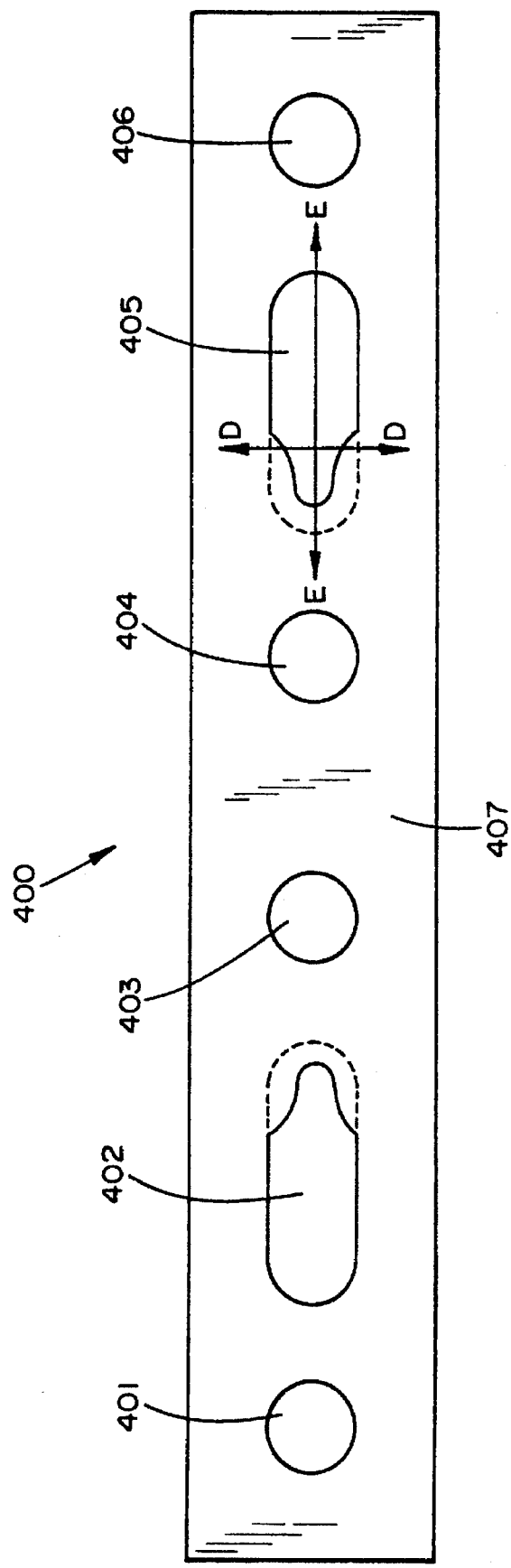
Figure 8B:
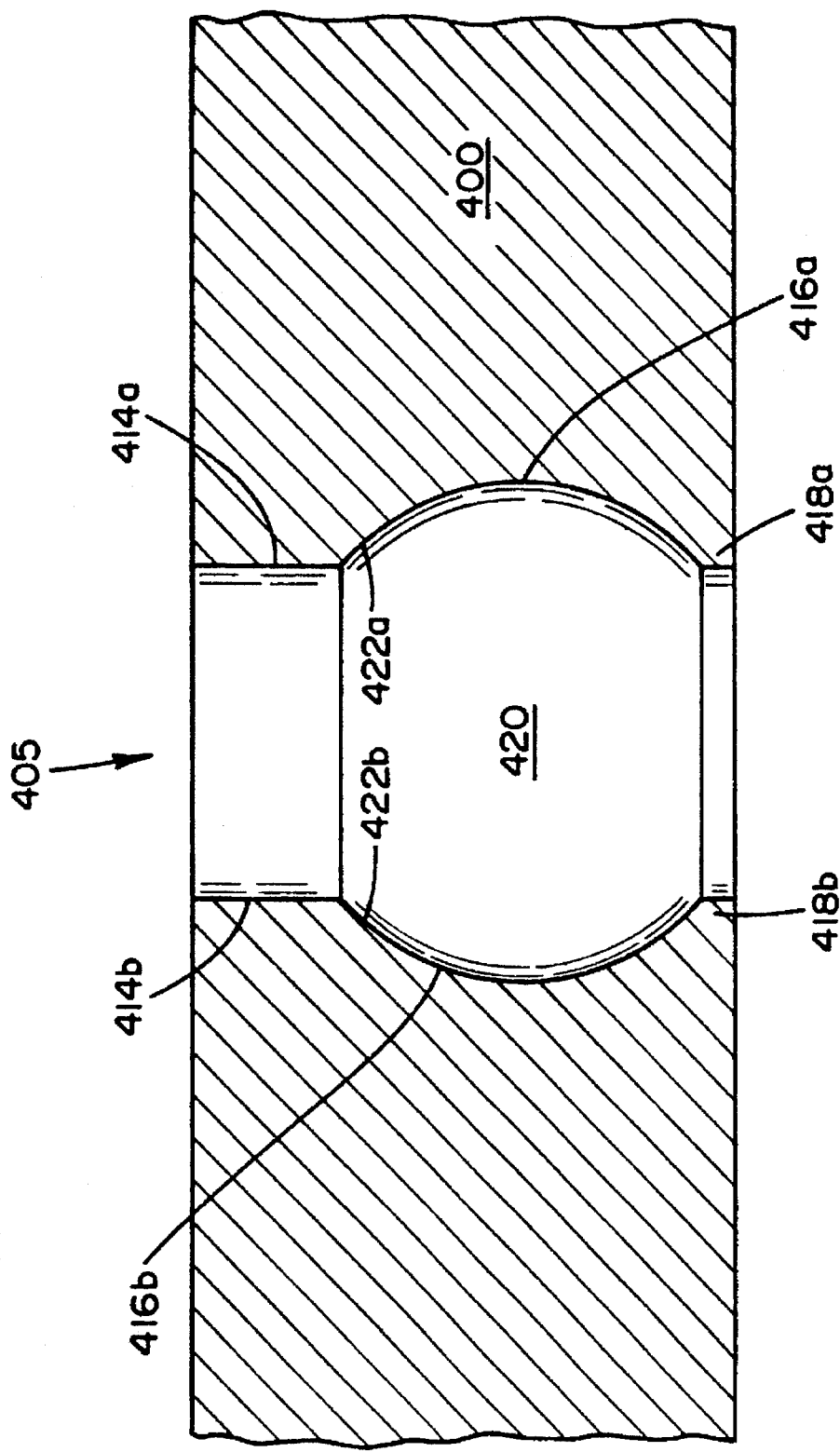
Figure 8C:
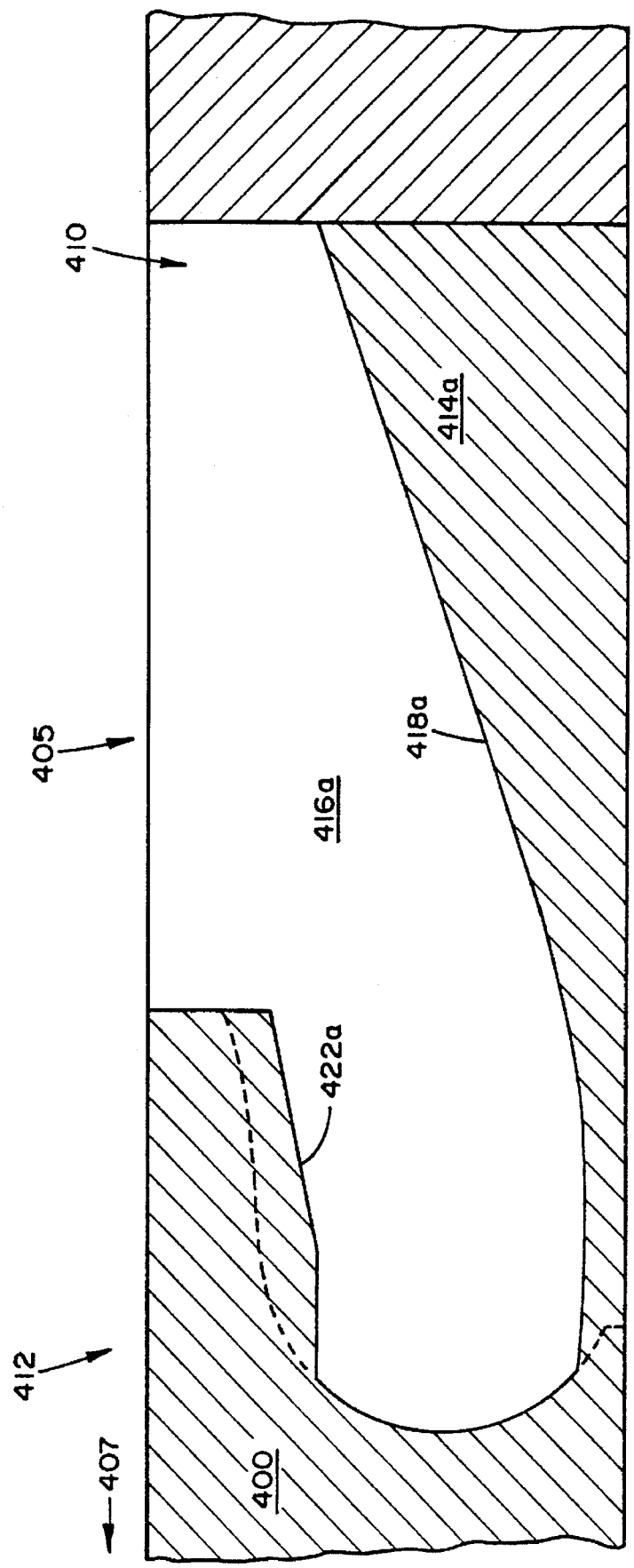

With reference now to FIGS. 8a, 8b, and 8c, in which the plate 400 of the third embodiment of the present invention is provided in a top view and two cross-sectional views (the cross-section views corresponding to the mutually perpendicular planes shown as axes D—D and E—E in FIG. 8a, respectively), a polyaxial locking dynamic compression plate assembly is provided which does not utilize a coupling element is described hereinbelow.

Referring specifically to FIG. 8a, the plate of the third embodiment is shown to comprise a series of holes 401–406; holes 401, 403, 404, and 406 being round and of the type used as described above and in the above-referenced co-pending application U.S. Ser. No. 08/421,087. Elongate holes 402 and 405 are positioned on the plate 400 on opposite sides of the middle 407 of the plate, similar to the gross plate configuration described above with respect to the first two embodiments.

Referring now also to FIGS. 8b and 8c, the specific conformation of the elongate holes is shown via mutually perpendicular cross-section views, taken along axes D—D and E—E shown in FIG. 8a. The remote ends 410 of the elongate holes 402, 405 are the portions of the holes which are farthest from the middle 407 of the plate. The proximal ends 412 of the holes are, conversely, the portion of the holes which are closest to the middle 407 of the plate 400. It is therefore understood that the elongate holes 402 and 405 are disposed in opposite orientation within plate 400.

Specifically referring to the morphology of the lateral sidewalls 414a and 414b of the elongate hole 405 (or 402), as shown in FIG. 8b, the sidewalls include concave portions 416a, 416b which curve inward, therein forming a pair of opposing lips 418a, 418b, which support the ball head 102 of the polyaxial screw 100 through a range of angles. The ball head 102 of the screw 100 is, therefore, disposed in a semi-spherical volume 420.

Referring now also to FIG. 8c, it is shown that the position of the concave curvate portion of the sidewalls 416a, 416b is dependent upon axial position in the hole 405. More specifically, the semi-spherical volume, and the lips 418a, 418b are sloped downward from the remote end 410 to the proximal end 412. Adjacent to the proximal end 412, the hole comprises a pair of upper lips 422a, 422b which provide for the securing of the screw within the plate.

Implantation of this embodiment of the present invention begins with the initial steps of positioning the plate 400 against the bone segments which the device is to compress together, and to which the assembly is to be secured, as set forth above with respect to the first two embodiments. Once positioned, with holes pre-drilled into the bone at ideal angulation, the screws 100 are inserted through the elongate holes 402 and 405. While this insertion is understood to occur for the purposes of drawing together the displaced bone segments to which the plate is affixed, the distance which the bones are drawn may be varied by insertion of the screws 100 along the open length of the elongate hole 402, 405.

The upper lips 422a, 422b prevent insertion of the screw directly through the proximal end of the hole in this embodiment, however, alternate means for locking the screw in place, for example a threaded cap (as disclosed in the co-pending, above-referenced, application, U.S. Ser. No. 08/421/087) may be provided.

Once initially driven into the bone, through the elongate hole 405, the head 102 of the screw 100 rests on the lower lips 418a, 418b, with the concave profile of the curvate sidewalls 416a, 416b securely supporting the head 102. Continued driving of the head into the bone causes the head to translate down the sloped lower lips 418a, 418b. As with the previous embodiments, this translation of the screw relative to the plate causes the bone segment into which the screw 100 is implanted to translate as well. The oppositely oriented elongate hole 402, and the second screw 100 is inserted therethrough, provide the opposing force for drawing the displaced bone segments together. At the proximal end 412 of the hole, the upper lips 422a, 422b are positioned to engage the head 102, and lock it into position as shown in FIG. 9.

Figure 9:
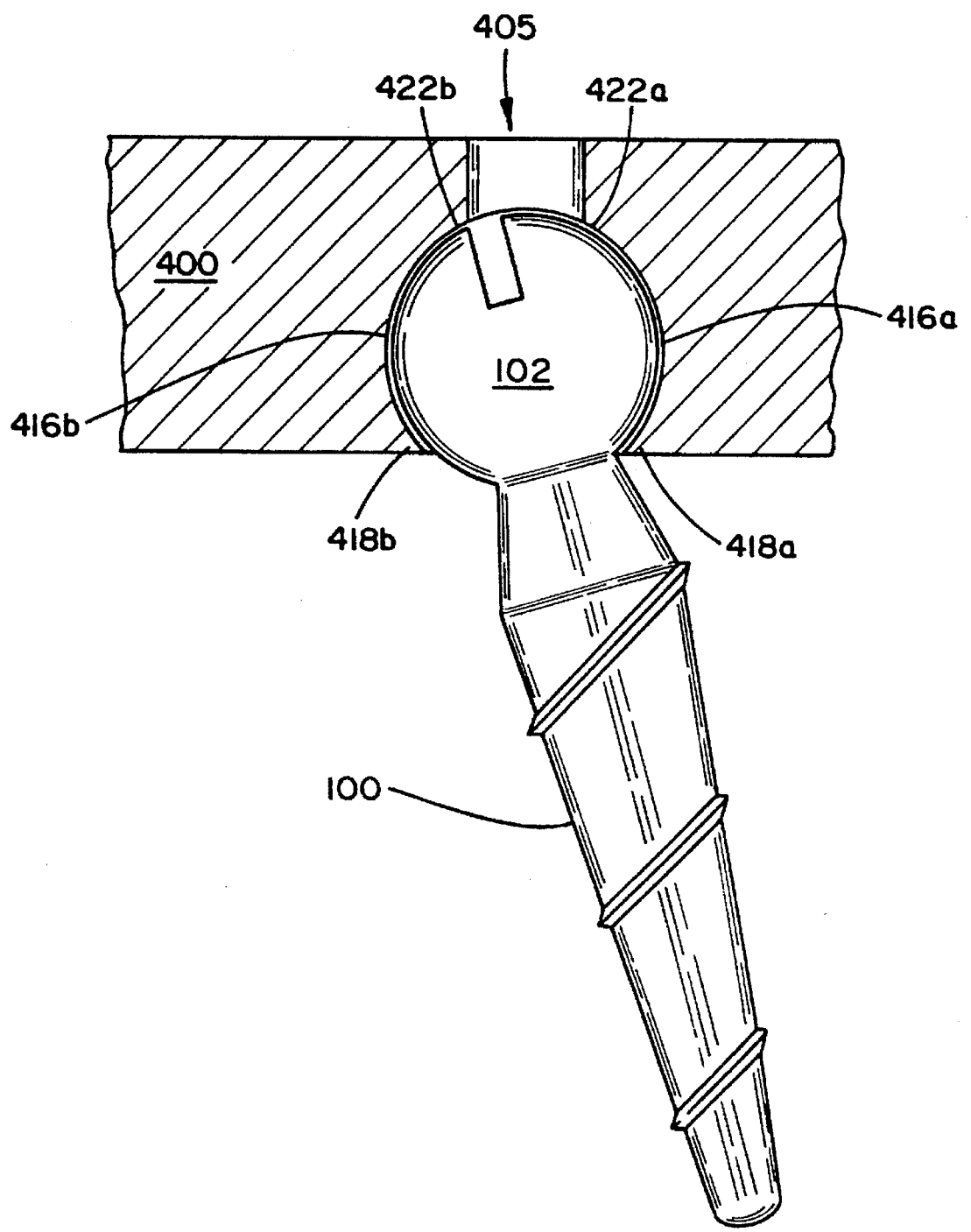
FIG. 9 is a side cross-section view of the seated and fully inserted implant assembly which is the third embodiment of the present invention.

More specifically, FIG. 9 shows a screw 100 which is fully inserted and locked at the proximal end 412 in the elongate hole 405 of the plate 400. The screw 100 retains its angulation throughout the process of bone segment compression, therein permitting the surgeon to provide maximum securing strength via non-perpendicular insertion, as well as preventing back-out by locking the screw 100 to the plate 400.

While there has been described and illustrated several embodiments of implantation devices for dynamically compressing adjacent displaced bone segments by affixing a dynamic compression plate which utilizes polyaxial locking screws to the bone segments, it will be apparent to those skilled in the art that variations and modifications are possible without deviating from the broad spirit and principle of the present invention which shall be limited solely by the scope of the claims appended hereto.

We claim:

1. A dynamic compression polyaxial locking screw plate assembly for drawing together and immobilizing a plurality of bone segments, via fixation to surfaces thereof, comprising:

an elongate plate including first and second longitudinal portions, and a middle defined therebetween;

at least one elongate hole, extending through at least one of said first and second longitudinal portions, having a remote end and a proximal end thereof and lateral sidewalls connecting said ends, each of said sidewalls including a sloped surface conformation;

means in at least the other of said first and second longitudinal portions by which said plate is securable to a first one of said plurality of said bone segments;

at least one corresponding coupling element, having a semi-spherical interior volume, said coupling element being insertable into said at least one elongate hole, slidable along said sloped surface conformations, and lockable within said elongate hole; and at least one corresponding bone screw having a semi-spherical head and a shaft, said shaft portion being insertable through the corresponding elongate hole and into a second one of said bone segments, and said semi-spherical head portion being rotationally freely mounted within the semi-spherical interior volume of the coupling element prior to insertion and such that the shaft of the bone screw and the coupling element may be inserted into the corresponding elongate hole and said shaft of the bone screw may be inserted into said second bone segment at a selected angle within a predetermined range of angles including non-perpendicular angles relative to the plate and thereby locking said coupling element and said semi-spherical head to said plate at said selected angle as said semi-spherical head and said coupling element are advanced into said elongate hole and along said sloped surface conformations toward the middle of said plate, thereby drawing the first and second bone segments together.

2. The dynamic compression polyaxial locking screw plate assembly as set forth in claim 1, wherein each of said ends of said plate comprises at least one elongate hole.

3. The dynamic compression polyaxial locking screw plate assembly as set forth in claim 1, wherein said plate further comprises at least one round hole, and wherein said means comprises a holding screw, insertable through said at least one round hole which provides added fixation strength.

4. The dynamic compression polyaxial locking screw plate assembly as set forth in claim 1, wherein a lower portion of the at least one coupling element comprises a plurality of slots which permit the interior semi-spherical volume to expand to receive said head portion of said screw therein, and to contract to crush lock to said head.

5. The dynamic compression polyaxial locking screw plate assembly as set forth in claim 1, wherein the at least one coupling element further comprises a single slot which extends the entire length of said coupling element, which permits the interior semi-spherical volume to expand to receive said semi-spherical head, and whereby inward radial force causes the single slot to close and the coupling element to crush lock to the semi-spherical head of the screw and compression lock within the elongate hole.

6. The dynamic compression polyaxial locking screw plate assembly as set forth in claim 1, wherein the surface conformations of the sidewalls of the at least one elongate hole comprise an axially widening taper, and wherein said coupling element has a corresponding axial taper.

7. The dynamic compression polyaxial locking screw plate assembly as set forth in claim 1, wherein the surface conformations of the sidewalls of the at least one elongate hole comprise an axially sloped channel, and wherein said coupling element has a corresponding annular flange.

8. The dynamic compression polyaxial locking screw plate assembly as set forth in claim 1, wherein the semi-spherical head portion of said screw comprises a recess to which a screwdriving tool is mateable for inserting said screw into said bone segment, and wherein the coupling element includes an opening in a top surface thereof, through which said screwdriving tool may access said recess of said screw.

9. A dynamic compression polyaxial locking screw plate assembly for drawing together and immobilizing a plurality of bone segments, via fixation to surfaces thereof, comprising:

an elongate plate including first and second longitudinal portions, and a middle defined therebetween;

at least one elongate hole, extending through at least one of said first and second longitudinal portions, having a remote end and a proximal end thereof and lateral sidewalls connecting said ends, each of said sidewalls including a sloped surface conformation and an axially sloped channel;

means in at least the other of said first and second longitudinal portions by which said plate is securable to a first one of said plurality of said bone segments;

at least one corresponding coupling element having an annular flange portion corresponding to said axially sloped channels, said coupling element being insertable into said at least one elongate hole, slidable along said sloped surface conformations with said annular flange portion seated within said axially sloped channels, and lockable within said elongate hole; and at least one corresponding bone screw having a head and a shaft, said head being rotationally coupled to one of said coupling element, and said shaft portion being insertable through the corresponding elongate hole and into a second one of said bone segments, whereby full insertion of said screw into said second bone segment causes said coupling element to slide down said sloped surface conformations and thereby drawing the first and second bone segments together.

* * * * *